United States Patent
Anikin

(10) Patent No.: US 7,603,913 B1
(45) Date of Patent: Oct. 20, 2009

(54) METHOD OF FINDING A THIGH SUPPORT HAVING GEOMETRY, RIGIDITY, AND ELASTICITY FOR MOST OPTIMAL BLOOD CIRCULATION IN THE LOWER EXTREMITIES OF A SEATED PERSON

(75) Inventor: Sergey Anikin, 87 Walnut Ave., Atherton, CA (US) 94027

(73) Assignee: Sergey Anikin, Atherton, CA (US)

( * ) Notice: Subject to any disclaimer, the term of this patent is extended or adjusted under 35 U.S.C. 154(b) by 0 days.

(21) Appl. No.: 12/151,547

(22) Filed: May 8, 2008

(51) Int. Cl.
*G01F 1/00* (2006.01)
*A47B 97/00* (2006.01)

(52) U.S. Cl. ............................ 73/861; 297/463.2

(58) Field of Classification Search ...... 73/861–861.69; 297/463.2
See application file for complete search history.

(56) References Cited

U.S. PATENT DOCUMENTS

| | | | | |
|---|---|---|---|---|
| 4,574,901 A | * | 3/1986 | Joyner | 180/65.1 |
| 4,636,002 A | | 1/1987 | Genjiro | |
| 4,712,834 A | | 12/1987 | Warrick | |
| 4,838,509 A | | 6/1989 | Klink et al. | |
| 4,840,425 A | * | 6/1989 | Noble | 297/284.1 |
| 5,083,551 A | | 1/1992 | Addison, Jr. | |
| 5,127,708 A | * | 7/1992 | Kishi et al. | 297/284.1 |
| 5,469,592 A | | 11/1995 | Johnson | |
| 6,015,394 A | * | 1/2000 | Young | 601/55 |
| 7,093,898 B2 | | 8/2006 | De Guevara | |
| 7,255,396 B1 | | 8/2007 | Anikin | |

FOREIGN PATENT DOCUMENTS

DE 102005002439 7/2006

OTHER PUBLICATIONS

U.S. Appl. No. 12/011,316, filed 2008, S. Anikin.
U.S. Appl. No. 11/509,376, filed 2006, S. Anikin.
U.S. Appl. No. 11/515,192, filed 2006, S. Anikin.
N. S. Lee, et al, "Review of Selected Literature Related to Seating Discomfort" submitted in 1990 to Ikeda Engineering Corporation, MI, USA.
Pain Releiver Co., KS, sells G-Seat Gel Seat Cushions described in Http://www.autosportcatalog.com/index.cfm/fa/p/pid/2168/cid/57/sc/2737 that are filled with a viscoelastic gel and are intended for redistribution of pressure on buttocks of a sitting person.
Direct Liquid Injection Subsystem Type DL125-C, Flow Measurement and Control (www.mksinst.com).

* cited by examiner

*Primary Examiner*—Andre J Allen
*Assistant Examiner*—Jermaine Jenkins

(57) ABSTRACT

A method of finding a thigh support for most optimal blood circulation in the lower extremities of a seated person consisting of measuring a blood-circulation parameter such as blood-flow velocity through the lower extremities of a seated person under different seating conditions, including those with or without the use of any thigh-supporting means. It has been proven that with the use of a thigh-supporting means, the measured blood-circulating parameter was much better than in a person seated without the use of a thigh-supporting means. Blood-flow velocity through the lower extremities of a person seated on the aforementioned seating device was measured by determining the Doppler shift in the frequency of returning ultrasound waves.

14 Claims, 4 Drawing Sheets

METHOD OF FINDING A THIGH SUPPORT HAVING GEOMETRY, RIGIDITY, AND ELASTICITY FOR MOST OPTIMAL BLOOD CIRCULATION IN THE LOWER EXTREMITIES OF A SEATED PERSON

FIELD OF THE INVENTION

The present invention relates to the field of ergonomics and, more specifically, to the method of finding a thigh support for the most optimal blood circulation in the lower extremities of a seated person.

BACKGROUND OF THE INVENTION

Sitting is the most frequent body posture: we sit at work, at school, in the car, on the bus, on the train, in an airplane, and so on. Those who are wheelchair-bound are in seated positions for an entire day.

A seat should take the weight off one's feet in order to lessen stress on the legs, and the seat should provide some postural stability while one works or relaxes. One should also be able to relax muscles that are at rest.

Seat height should not be so high that the occupant's legs are left dangling. This would mean that there would be pressure on the soft tissues under the thighs. This pressure can interfere with the return of blood from the lower limbs, which may cause tingling and numbness in the thighs due to pressure on blood vessels and nerves.

At the same time, there exists an opinion that prolonged travel in a seated position can cause venous stasis, which means loss of proper function of the veins that carry blood back to the heart from a person's legs.

N. S. Lee, et al, showed in their "Review of Selected Literature Related to Seating Discomfort" submitted in 1990 to Ikeda Engineering Corporation, Mich., USA, that in terms of ml/min/100 ml of body segment, blood flow in the leg of a person (4 ml/min/100 ml) in a seated position is much lower than, e.g., in the arm (10 ml/min/100 ml). This means that the legs of a seated person are to a greater extent subject to tingling and numbness in the thighs caused by pressure on blood vessels and nerves.

It is understood that in the body of a person seated on a chair or on a similar support, the aforementioned abnormalities of blood circulation are caused by areas on the chair that cause increased pressure on the thighs. In the majority of cases, such areas are the edges of a seat.

Attempts have been made to improve a seat support for redistribution of pressure on the buttocks. For example, Pain Reliever Co., KS, distributes a G-Seat Gel Cushion (hereinafter referred to as "G-Seat Gel Cushion") for improved blood circulation. (See Http://www.autosportcatalog.com/index-.cfm/fa/p/pid/2168/cid/57/sc/2737)

The G-Seat Gel Cushion uses viscoelastic gel and a functional design to disperse pressure and to improve the level of comfort wherever one is seated. The G-Seat Gel Cushion features a center relief groove that eliminates soft-tissue compression and suspends the tailbone (coccyx), therefore eliminating direct pressure on the spine.

Pressure redistribution occurs because the gel that fills the seat works like a liquid and conforms to the body part, i.e., the buttocks. In other words, pressure on the buttocks and thigh surfaces in contact with the G-seat Gel Cushion is redistributed in accordance with Pascal's Law, i.e., in a normal direction and essentially uniformly at all points of contact. However, since the G-seat Gel Cushion is substantially flat, the problem is solved only partially. In other words, localized areas of increased pressure will still exist on the boundaries of the G-seat Gel Cushion.

German Patent Publication DE10200500243 published on Jul. 27, 2006 (inventor A. Wunder, et al) discloses a chair with a seat that has a backrest, cushion, and adjustable thigh support. The thigh support comprises a U-shaped unit that is arranged across the chair under the thighs of the occupant and is adjustable opposite the cushion. A gap is formed between the cushion and the U-shaped unit during adjustment of the U-shaped unit opposite to the cushion. The gap is coverable by an adjustment device, and the cushion is composed of a foam material. The above-described thigh support does not solve the aforementioned problem of localized pressure on the thigh surfaces at the edge of the transverse thigh support and, instead, only shifts the position of the edge.

A number of patents, such as U.S. Pat. No. 4,636,002 (published on Jan. 13, 1987, inventor T. Genjiro), U.S. Pat. No. 4,712,834 (published on Dec. 15, 1987, inventor J. Warrick, et al), and U.S. Pat. No. 4,838,509 (published on Jun. 13, 1989, inventor J. Klink, et al), etc., disclose car seats with adjustable features that include thigh supports. However, all of these devices are permanently built into the structure of the seat, operate with the use of complicated and expensive mechanisms, and change only vertical and angular positions of the transverse thigh support.

U.S. Pat. No. 5,083,551 issued in 1992 to K. Addison, Jr. discloses a method and apparatus for providing improved blood circulation to a person seated in a wheelchair or stationary chair used by handicapped persons, or by those who must remain inactive in a seated position for extended periods of time. The apparatus imparts an undulating, wave-like motion to the flexible seat portion of the chair which stimulates circulation of blood in the lower extremities and prevents development of ischemic or decubitus ulcers by providing changing points of pressure on the buttocks and thighs of a seated individual. The apparatus is connected to a wheelchair or chair and is powered by a storage battery mounted thereon.

U.S. Pat. No. 7,093,898 issued in 2006 to L. De Guevara discloses a portable air-pressure-applying assembly for seats. Proposed in this patent is an air-pressure-applying assembly for a seat, having an occupant-holding portion for selectively applying the desired pressure to the body of the seated occupant. This assembly includes an air-bag assembly, an air-pressure source, an inlet-conduit assembly, an exhaust valve assembly, and a control assembly. The air-bag assembly is removably attached to the seat occupant-holding portion. The inlet-conduit assembly is in fluid communication at one end with the air-pressure source and at another source with the air-bag assembly. The exhaust valve assembly is in fluid communication at one end with the inlet conduit assembly and has an air outlet at the other end. A control assembly is linked to the air pressure source and to the exhaust valve assembly. The control assembly is configured so as to selectively signal the air-pressure source to inflate the air bag assembly in order to apply the desired pressure to the body of the seat occupant and to selectively signal the exhaust valve assembly to release air from the air-bag assembly.

In order to solve the above problem, the inventor herein has developed a pad for supporting the thigh of a person seated on a seat in a position that alleviates pressure applied to the lower surface of the thigh and thus for improving blood circulation through the leg without numbness or similar phenomena associated with long-time sitting. This pad is disclosed in U.S. Pat. No. 7,255,396 issued to the applicant of the present patent application in 2007. The pad is made in the form of a soft deformable body filled, e.g., with silicone gel. The pad has a flat rectangular bottom surface and curvilinear lateral sides. In the plane perpendicular to the bottom, the pad has a triangular cross-section with heights of the triangles gradually reduced from one end face of the pad to the opposite end face of the pad so that the ridge that connects the apexes of the triangular cross-sections from one end face to the other is inclined with respect to the flat bottom.

In further development of the above idea, the applicant of the present patent application invented a self-inflatable thigh support, which is disclosed in pending U.S. patent application Ser. No. 12/011,316 filed on Jan. 26, 2008. The thigh support is made in the form of an elongated body of a triangular cross-section that consists of an airproof inner casing made from a nonstretchable flexible material and a squeezable foam plastic that fills the interior of the casing. The casing is provided with a valve that can be opened for squeezing the pad to the compressed state and then closed for preserving the pad in the compressed state, which is convenient for storage and transportation. To use the pad, the valve is opened, the squeezed foam plastic is expanded, and then the valve is closed, whereby the pad is maintained in a predetermined shape and with a predetermined rigidity. An advantage of this thigh support is that it can be deflated and squeezed to small dimensions that are convenient for storage and transportation. Another advantage is that rigidity of the support in the inflated state can be adjusted by releasing a portion of air trapped in the fully inflated thigh support.

It has been stated in the aforementioned pending patent application that the use of a thigh support of the aforementioned type alleviates pressure applied to the lower surface of the thigh and thus improves blood circulation through the leg without numbness or similar phenomena associated with long-time sitting. However, this statement is qualitative because no one has tried to measure the degree to which use of such support can improve blood circulation in the legs of a seated person nor the geometry, rigidity, or elasticity required of such thigh support for the most optimal blood circulation.

OBJECTS AND SUMMARY OF THE INVENTION

It is an object of the present invention to provide a method for quantitatively proving that use of a thigh support improves blood circulation of a seated person as compared to the condition of a seated person without use of the thigh support. It is a further object to find a thigh support of optimal geometry, rigidity, and elasticity from the viewpoint of blood circulation in the legs of a seated person.

The method of the invention comprises the following steps: providing an instrument capable of measuring parameters of blood circulation through the lower extremities of a seated person; providing a chair for measuring the circulation of blood through the lower extremities of a person; measuring blood circulation parameters in the lower extremities of a group of individuals when each individual sits on the aforementioned chair without the use of any thigh-supporting means; calculating the average value of measured parameters for a person sitting without thigh supports; providing a group of thigh supports of various geometry, rigidity, and elasticity; repeating the aforementioned measurement for each individual with use of the aforementioned thigh supports; calculating the average value of the measured parameter for thigh supports of each specific geometry, rigidity, elasticity, and combinations thereof; and finding a thigh support of such geometry, rigidity, and elasticity that produces the best blood circulation parameter.

An instrument that is suitable for realization of the proposed method is, for example, the Siemens ultrasound machine SONOLINE G60 S, which controls programmable imaging parameters, exam steps, and measurement and report packages. The data are obtained in the form of computerized images that are easy to interpret and compare. In other words, output data of the aforementioned instrument show variation of such parameters as blood-flow velocity passing through selected organs of the body, which, in the case of the present invention, are the lower extremities.

The method involves a technique wherein a piezoelectric ultrasound transducer is placed in the legs of an individual. Ultrasound waves then are transmitted toward the path of blood flow in the legs and are reflected and received. Measurement is based on the Doppler frequency difference between transmitted and received waves is normally used for measuring cardiac output, which is the volume of blood being pumped by the heart, in particular, the output of a ventricle in one minute. This method uses ultrasound and the Doppler effect to measure CO. Blood velocity through the heart causes a Doppler shift in the frequency of the returning ultrasound waves. This Doppler shift can then be used to calculate flow velocity and volume and effective CO [cardiac output] using the following equations:

$$CO = SV \times HR$$

$$SV = vti \times CSA$$

where:
CSA=flow cross sectional area from $\pi d^2/4$
d=valve diameter
vti=velocity time integral of the trace of Doppler flow profile In the method of the invention, the same principle is used to measure velocity of blood flow passing through the arteries and veins of the legs in a person examined for the effect of the thigh support.

Such a method is described, e.g., in U.S. Pat. No. 7,147,602 issued in 2006 to Muramatsu, et al. This patent describes a blood-rheology-measuring apparatus comprising means for noninvasively detecting the velocity of blood flow in a blood vessel as a Doppler shift signal by transmitting and receiving a wave from the face of the skin. The apparatus contains means for analyzing blood rheology from a temporal change in value of blood-flow velocity. The device is portable and capable of simply measuring blood rheology even outside a medical institution without applying burden on a subject.

DETAILED DESCRIPTION OF THE INVENTION

The present invention is based on measuring the velocity of blood flow through the lower extremities of a seated person in order to prove that the thigh-support pillow developed by the inventor and disclosed in U.S. Pat. No. 7,255,396 improves blood-circulation conditions as compared with the same person seated on the same seat but without the use of the aforementioned thigh support. The main purpose of the present invention is to provide a method for finding the optimal geometry, rigidity, and elasticity for the aforementioned thigh-support pillow from the viewpoint of blood-circulation conditions.

More specifically, the method of the invention consists of the following. First, an instrument is selected based on the capability of measuring parameters of blood circulation through the lower extremities of a seated person. A variety of such instruments is known. For example, this may be the device described in U.S. Pat. No. 7,147,602 issued in 2006 to Muramatsu, et al. This patent describes a blood-rheology-measuring apparatus comprising means for noninvasively detecting blood-flow velocity in a blood vessel as a Doppler shift signal by transmitting and receiving a wave from the face of the skin and means for analyzing blood rheology from a temporal change in the flow velocity of the blood detected by a portable device which is capable of simply measuring blood rheology anywhere even outside of a medical institution without applying burden on a subject. Another method and device suitable for measuring the blood flow circulating though the lower extremities of a person are disclosed in U.S. Pat. No. 6,868,739 issued in 2005 to Krivitski, et al. A known change is made to the flow to be measured, resulting changes (or values corresponding to these changes), or relative changes in the flow to be measured are monitored, and the initial flow in the conduit is calculated from the value of the known change and monitored changes. Devices that can be used to practice the method include catheters having one or two sensors and one or two sites for introducing volume change.

However, the inventor has chosen the Siemens ultrasound SONOLINE G60 S, which controls programmable imaging parameters, exam steps, and measurement and report packages. The data are obtained in the form of computerized images that are easy to interpret and compare. In other words, output data of the aforementioned instrument show variations in blood-flow velocity passing through the selected organs of a body, which, in the case of the present invention, are the lower extremities.

Figure 1:
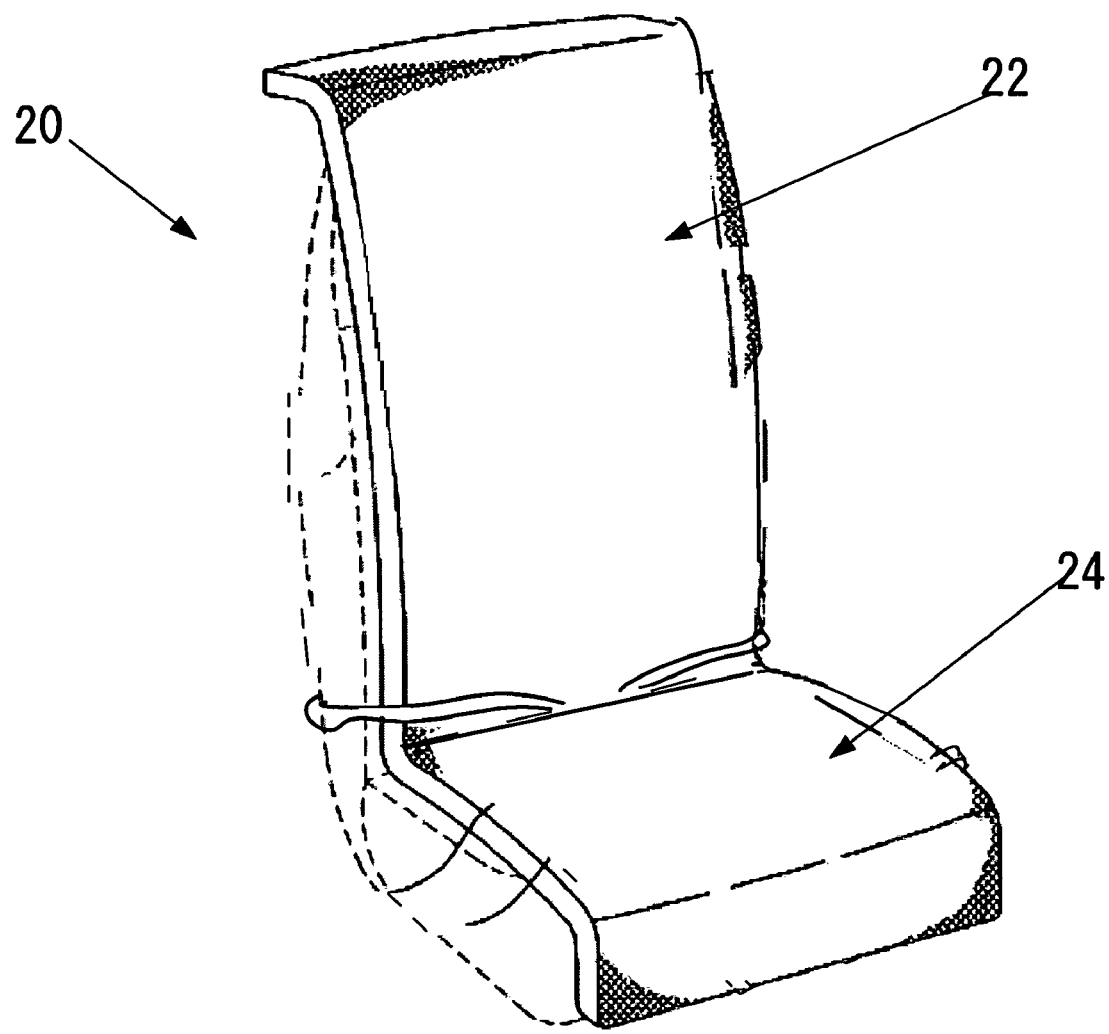
FIG. 1 is a three-dimensional view of an aircraft chair selected for carrying out the method of the invention.

The next step is to provide a chair with a seat suitable for measuring the circulation of blood through the lower extremities of a person. This may be a car seat, an airplane seat, a wheelchair, an armchair of the type used in offices, i.e., a seat of the type in which a person spends a substantial time in a seated position. The chair selected for the test is an aircraft chair 20 of the type shown in FIG. 1. The chair 20 has a backrest 22 and a seat 24.

The next step is measuring blood circulation parameters in the lower extremities of a group of individuals when each individual is seated on the aforementioned chair without the use of any thigh-supporting means. Measurements are carried out by means of the aforementioned Siemens ultrasound SONOLINE G60 S and the L10-5 transducer (not shown).

First, measurements of the blood circulation parameters are carried out for individuals seated on the selected seat 24 without the use of a thigh support, and then an average value of the measured parameters is calculated.

Figure 2:
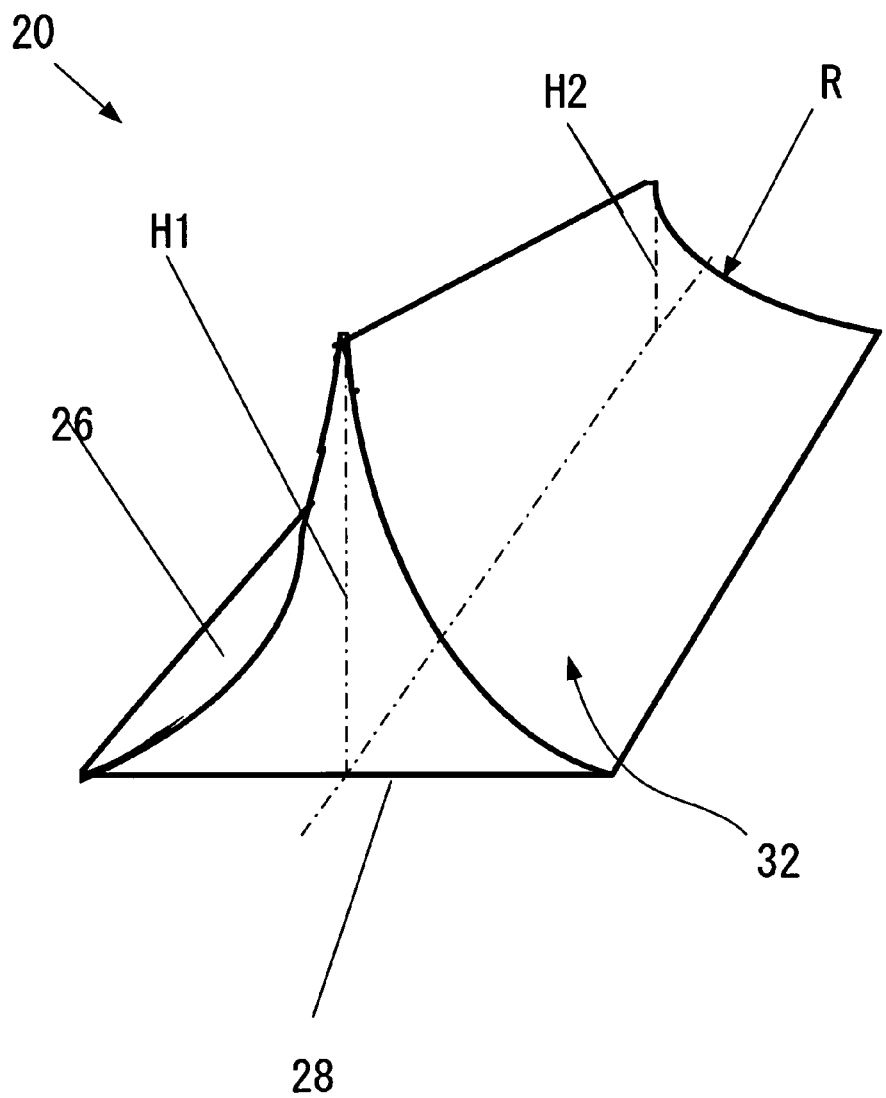
FIG. 2 is a three-dimensional view of a thigh-supporting pad used in the method of the invention.

Following this, a group of thigh supports of different geometry, rigidity, and elasticity is selected. In the test conducted by the inventor, two basic thigh supports were used. A thigh support of the first type is one disclosed in U.S. Pat. No. 7,255,396 issued to the applicant of the present application (S. Anikin) in 2007 under the title, "Ergonomic thigh support and method of uniformly distributing pressure on the thigh surface of a seated person." The pad described in U.S. Pat. No. 7,255,396 is shown in FIG. 2. The pad, which is designated by reference numeral 26, is intended to support the thigh of a person seated (not shown in FIG. 2) in a position that alleviates pressure applied to the lower surface of the thigh and thus improves blood circulation through the leg without numbness or similar phenomena associated with long-time sitting.

For test and evaluation purposes, only one thigh support can be used, e.g., under the right thigh, although in practice two thigh supports should be used for improving blood circulation in both legs of the user.

The pad 26 shown in FIG. 2 is made in the form of a soft deformable body filled, e.g., with silicone gel. The pad has a flat rectangular bottom surface 28 and curvilinear lateral sides 30 and 32. In the plane perpendicular to the bottom 28, the pad 26 has a triangular cross-section with heights H1 and H2 of the triangles gradually reduced from one end face of the pad to the opposite end face of the pad so that the ridge 34 that connects the apexes of the triangular cross-sections from one end face to the other is inclined with respect to the flat bottom 28.

Among the geometrical parameters of this pad, the following were changes: height H1, height H2, and radius of curvature R. Ten pads with different sets of dimensions Y1, H2, and R1 were produced for the test.

A thigh support of the second type was a self-inflatable under-thigh support disclosed in pending patent application Ser. No. 12/011,316 filed by the same applicant on Jan. 26, 2008. The thigh support of this type is produced by Traffic Pillow Inc., California, under the trademarks Traffic Pillow® and Travel Pillow™.

Figure 3:
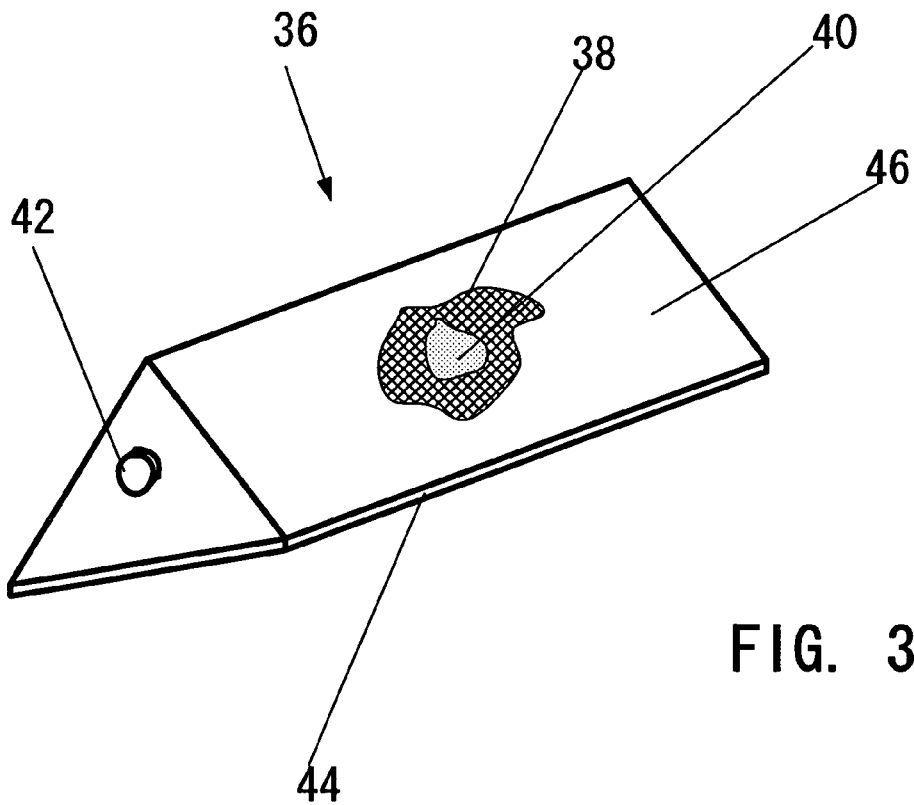
FIG. 3 is a three-dimensional view of a self-inflatable thigh-supporting pad used in the method of the invention.

The aforementioned self-inflatable under-thigh support 36, which is shown in FIG. 3, is intended for use in combination with a car seat for use by a driver of a vehicle in order to shorten brake-activation reaction time and to reduce pressure on the lower side of the thigh in order to improve blood circulation. The under-thigh support 36 is made in the form of an elongated body of a triangular cross-section that consists of an airproof inner casing 38 made from a nonstretchable flexible material and a squeezable foam plastic 40 (FIG. 3) that fills the interior of the casing 38. The casing 38 is provided with a valve 42 that can be opened for squeezing the pad to the compressed state and then closed for preserving the pad in the compressed state, which is convenient for storage and transportation. To use the pad 36, the valve 42 is opened, the squeezed foam plastic is expanded, and then the valve is closed, whereby the pad is maintained in a predetermined shape and with a predetermined rigidity.

The terms rigidity and elasticity in the present patent specification refer to values that are measured according to the methods described below.

Figure 4:
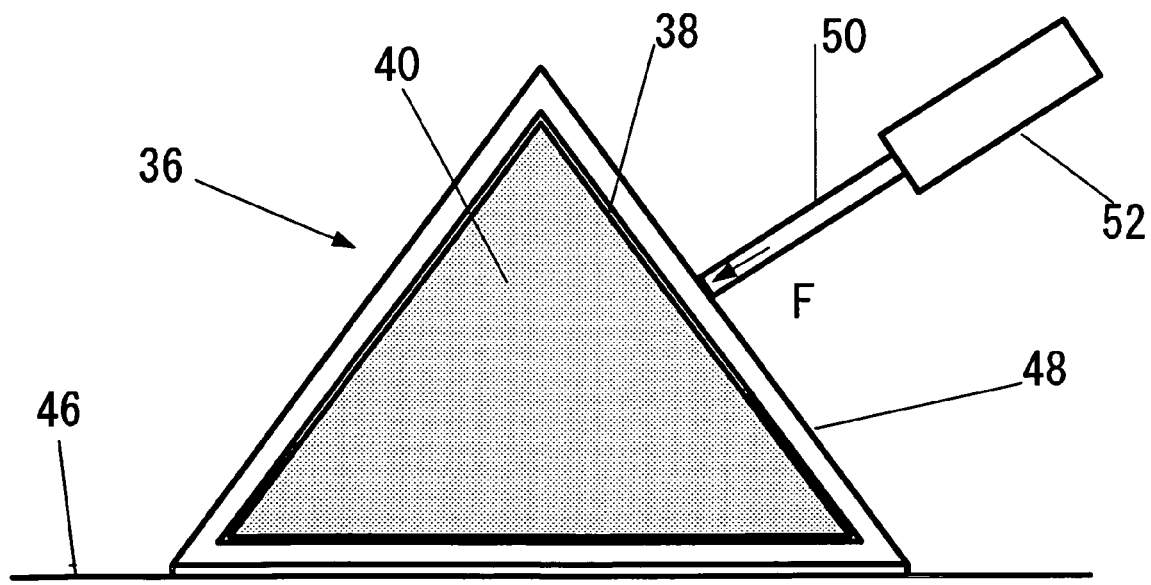
FIG. 4 is a sectional view of the pad of FIG. 3 illustrating measurement of rigidity and elasticity of the thigh-supporting pad.

What is meant by rigidity is the length of the stroke by a probe that is applied at a constant force to the surface of the pad. More specifically, rigidity was measured by placing the pad 36 with its support surface 44 on a rigid plate 46 (FIG. 4), applying a constant force F, e.g., 1 N, in the direction perpendicular to a side surface 48 of the pad from a probe 50 of a loading device 52, and measuring the length of the probe stroke. FIG. 4 is a transverse cross-section of the pad 60 in the direction perpendicular to the support surface 44. For comparison of rigidity values of pads 36 with varying amounts of pressure of air trapped inside the airproof inner casing 38 (FIGS. 3 and 4), the length of the stroke of the probe 50 was measured during application of aforementioned force of 1 N. The shorter is the stroke, the higher is the rigidity.

Elasticity is determined by measuring the distance required for point of contact of the pad 36 with the probe 50 to return to a free state after release from contact with the probe 50. The greater is the distance, the higher is the elasticity.

Figure 5:
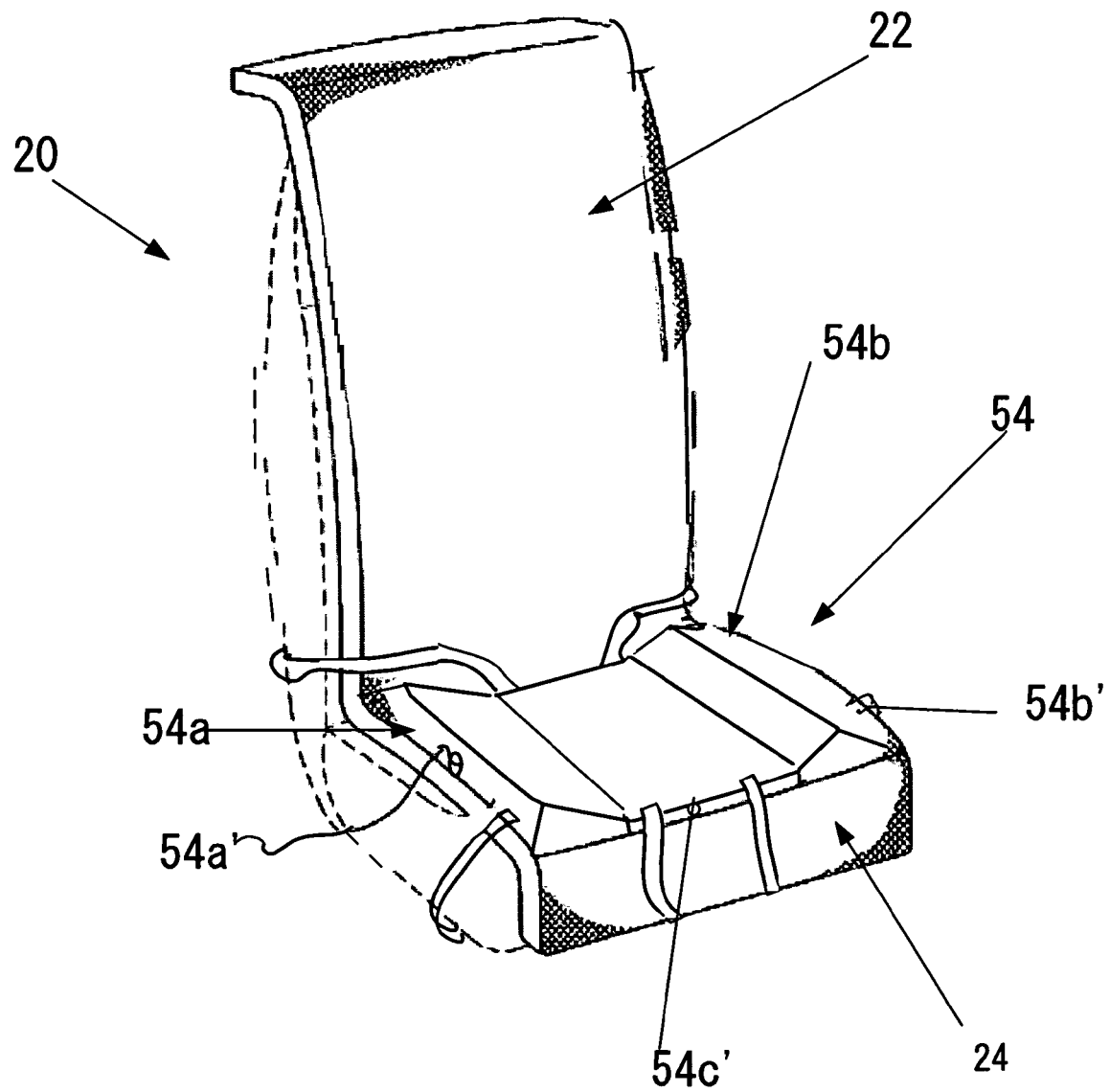
FIG. 5 is a three-dimensional view of a chair of FIG. 1 illustrating position of the thigh-supporting pads on the chair for testing effect of the pads on blood circulation in the legs of a seated person.

The test was conducted with the use of a multisectional thigh-support device 54 shown in FIG. 5 that illustrates the position of the device 54 on a seat 24 of the aircraft chair 20. The thigh-support device 54 consists of two self-inflatable sections 54a and 54b for supporting the right and left thighs of a user, respectively, and with an intermediate self-inflatable section 54c therebetween. Each section can be self-inflated by locking the air that is trapped in the sections 54a, 54b, and 54c to a predetermined rigidity and elasticity. The section 54c can be deflated so as not to interfere with the results of the thigh-support tests. Reference numerals 54a', 54b', and 54c' designate valves of respective sections.

The aforementioned tests to measure blood-flow velocity passing through the arteries and veins of the user's legs were conducted for a number of people, e.g., for ten individuals and under the same conditions for each person, and then the average value of the measured parameters was calculated for the thigh support 36 (FIG. 3) or for the thigh-support device 54 (FIG. 5) of each specific geometry, rigidity, elasticity, or combination thereof. The term same condition means, e.g., that prior to measurement, each person sits in the same position for the same amount of time and in the same chair, armchair, wheelchair, etc.

The method described above makes it possible to find a thigh support of such geometry, rigidity, and elasticity that produces the best blood-circulation parameter. Furthermore, it has been proven that use of a thigh-supporting means, such as the thigh support produced by Traffic Pillow Inc., California, under trademarks Traffic Pillow® and Travel Pillow™, significantly improves blood-circulation conditions in the extremities of a seated person, as compared to the conditions of a seated person without use of these thigh-supporting means.

Thus, it has been shown that the present invention provides a method for quantitatively proving that use of a thigh support improves blood circulation of a seated person as compared to the condition when this person is seated without use of a thigh support. The method allows finding a thigh support of the geometry, rigidity, and elasticity most optimal from the viewpoint of blood circulation in the legs of a seated person.

Although the invention has been shown and described with reference to specific examples, it is understood that these examples should not be construed as limiting the invention and that any changes and modifications can be made with regard to materials, shapes, and other features of the illustrated embodiments without departure from the scope of the patent claims. For example, the method of the invention can be used for ergonomically designing chairs, armchairs, seats, wheelchairs, desks, driver's seats, or any other seating devices for use with or without thigh supports. It is understood that the above method is applicable for measuring velocity of blood circulation not necessarily in the lower extremities but in any organs of a living body. Instruments and methods mentioned for measuring blood circulation parameters or devices and methods for evaluating rigidity and elasticity of the supports may differ from those mentioned in the specification. For example, a self-heated thermistor technique can be used to measure blood flow from a tissue surface. Intragraft blood flow can be measured by means of the Angioflow™ meter, which is an accurate and reliable endovascular measurement device. Blood flow can also be measured with use of a monochromatic laser diode by inserting a laser probe into tissue for depicting a small portion of scattered light that reflects back to the probe. Blood flow can be measured with hemodialysis shunts by injecting an indicator material into a venous line leading from the dialysis equipment to the shunt. Blood flow in an arterial line leading from a shunt at a location downstream of the venous line to the dialysis equipment can be monitored by an arterial line sensor for the presence of indicator material.

The invention claimed is:

1. The method for finding thigh-support means for most optimal blood circulation in the lower extremities of a seated person comprises the following steps:
   providing an instrument capable of measuring at least one blood circulation parameter for blood flow circulating through the lower extremities of a seated person;
   providing a seating device for use in measuring the circulation of blood through the lower extremities of a person;
   measuring the aforementioned at least one blood circulation parameter in the lower extremities of a group of individuals when each individual sits on the aforementioned seating device without use of thigh-supporting means;
   calculating the average value of the measured blood circulation parameters for a seated person without use of thigh-supporting means;
   providing thigh-supporting means of varying geometry, rigidity, and elasticity;
   repeating the aforementioned measurement for each individual with use of the aforementioned thigh-supporting means;
   calculating the average value of the aforementioned blood-circulation parameter for thigh-supporting means of each specific geometry, rigidity, elasticity, or combination thereof; and
   finding thigh-supporting means of a geometry, rigidity, and elasticity that produces the most optimal blood-circulation parameter.

2. The method of claim 1, wherein the step of measuring the aforementioned at least one blood-circulation parameter is carried out by using a pressure-sensitive instrument.

3. The method of claim 2, wherein the step of measuring the aforementioned at least one blood-circulation parameter is blood-flow velocity through the lower extremities of the person seated on the aforementioned seating device.

4. The method of claim 3, wherein blood-flow velocity through the lower extremities of the person seated on the aforementioned seating device is measured by determining the Doppler shift in the frequency of returning ultrasound waves.

5. The method of claim 1, wherein the step of measuring the aforementioned at least one blood-circulation parameter is blood-flow velocity through the lower extremities of the person seated on the aforementioned seating device.

6. The method of claim 5, wherein blood-flow velocity through the lower extremities of the person sitting on the aforementioned sitting device is measured by determining the Doppler shift in the frequency of returning ultrasound waves.

7. The method of claim 6, wherein the thigh-supporting means comprise an under-thigh support in the form of a soft deformable body having a flat bottom surface, curvilinear lateral sides, and a triangular cross-section in the plane perpendicular to the bottom surface, with the height of the triangular cross section gradually reduced from one end face of the under-thigh support to the other end face.

8. The method of claim 7, wherein the thigh-supporting means of each specific geometry, rigidity, elasticity, or combinations thereof are obtained by using thigh-supporting means having different heights of the triangular cross sections on the end faces and radii of curvature on the aforementioned curvilinear lateral sides.

9. The method of claim 6, wherein the thigh-supporting means comprise a self-inflatable body of a triangular cross-section that consists of an airproof inner casing made from a nonstretchable flexible material and a squeezable foam plastic that fills the interior of the casing, the casing being provided with a valve that can be opened for squeezing the pad to the compressed state and can then be closed for preserving the pad in the compressed state, which is convenient for storage and transportation.

10. The method of claim 1, wherein the thigh-supporting means comprise an under-thigh support in the form of a soft deformable body having a flat bottom surface, curvilinear lateral sides, and a triangular cross section in the plane perpendicular to the bottom surface, with the height of the triangular cross section gradually reduced from one end face of the under-thigh support to the other end face.

11. The method of claim 10, wherein the thigh-supporting means of each specific geometry, rigidity, elasticity, or combination thereof are obtained by using thigh-supporting means having different heights of the triangular cross sections on the end faces and radii of curvature on the aforementioned curvilinear lateral sides.

12. The method of claim 1, wherein the thigh-supporting means comprise a self-inflatable body of a triangular cross-section that consists of an airproof inner casing made from a nonstretchable flexible material and a squeezable foam plastic that fills the interior of the casing, the casing being provided with a valve that can be opened for squeezing the pad to the compressed state and can then be closed for preserving the pad in the compressed state, which is convenient for storage and transportation.

13. The method of claim 12, wherein rigidity and elasticity of the self-inflatable body is varied by changing the amount of air entrapped inside the airproof inner casing.

14. The method of claim 13, wherein rigidity and elasticity of the self-inflatable body is varied by changing the amount of air entrapped inside the airproof inner casing.

* * * * *